United States Patent
Busujima

(10) Patent No.: US 8,083,999 B2
(45) Date of Patent: Dec. 27, 2011

(54) STERILIZING APPARATUS

(75) Inventor: Hiroki Busujima, Ota (JP)

(73) Assignee: Sanyo Electric Co., Ltd., Moriguchi-shi (JP)

( * ) Notice: Subject to any disclaimer, the term of this patent is extended or adjusted under 35 U.S.C. 154(b) by 400 days.

(21) Appl. No.: 12/294,161

(22) PCT Filed: Mar. 8, 2007

(86) PCT No.: PCT/JP2007/054537
§ 371 (c)(1),
(2), (4) Date: Mar. 3, 2009

(87) PCT Pub. No.: WO2007/111106
PCT Pub. Date: Oct. 4, 2007

(65) Prior Publication Data
US 2009/0185960 A1    Jul. 23, 2009

(30) Foreign Application Priority Data

Mar. 27, 2006    (JP) .................................. 2006-085902

(51) Int. Cl.
*A61L 9/00*    (2006.01)
*A61L 2/00*    (2006.01)
*B06B 1/00*    (2006.01)

(52) U.S. Cl. ................ 422/298; 422/1; 422/28; 422/30; 422/127; 422/292; 422/305; 422/307

(58) Field of Classification Search ................ 422/1, 28, 422/30, 127, 292, 298, 305, 307
See application file for complete search history.

(56) References Cited

U.S. PATENT DOCUMENTS

| | | | |
|---|---|---|---|
| 5,091,107 A * | 2/1992 | Hutchings | 252/187.21 |
| 6,585,943 B1 * | 7/2003 | Sanford et al. | 422/307 |
| 2004/0005240 A1 * | 1/2004 | Adiga et al. | 422/1 |

FOREIGN PATENT DOCUMENTS

| | | | |
|---|---|---|---|
| JP | 64-25865 | | 1/1989 |
| JP | 2005-143726 A | * | 9/2005 |
| WO | WO 2005/046742 A1 | | 5/2005 |
| WO | WO 2006/016620 A1 | | 2/2006 |

OTHER PUBLICATIONS

English Translation of the "Drawings" and the "Detailed Description" sections of JP 2005-143726 A.*
Supplementary European Search Report dated Apr. 23, 2010.

* cited by examiner

*Primary Examiner* — Jill Warden
*Assistant Examiner* — Monzer Chorbaji
(74) *Attorney, Agent, or Firm* — Kratz, Quintos & Hanson, LLP

(57) ABSTRACT

There is provided a sterilizing apparatus which is capable of sterilizing articles, such as test tubes, flasks, beakers, scalpels, forceps and so on, with high efficiency in a short time. The sterilizing apparatus includes a sterilizing gas generator 42 that supplies sterilizing gas into a chamber 4. The sterilizing gas generator 42 atomizes a sterilizer solution (oxygenated water) by means of an ultrasonic vibrator 46. The sterilizing apparatus further includes an ultraviolet generator (ultraviolet lamp 50) that irradiates gas in the chamber 4 with an ultraviolet ray. The sterilizing apparatus further includes a door 14 for blocking an opening 2A of the chamber 4 in a free-opening/closing manner and a locking device 52 for prohibiting the door 14 from being opened. The sterilizing apparatus further includes a controller 60 for controlling the locking device 52 to prevent the door 14 from being opened from start of the sterilization process to end of the decomposition process.

2 Claims, 2 Drawing Sheets

STERILIZING APPARATUS

BACKGROUND OF THE INVENTION

This invention relates to a sterilizing apparatus for sterilizing articles received in a chamber.

In the related art, when articles such as vessels are to be cleaned, a water/air mixture is sprayed into the articles by means of a water/air mixture spraying device, distilled water is sprayed into the articles by means of a distilled water spraying device, and then sterile water is sprayed into the articles by means of a sterile air spraying device. In that manner, the articles are sterilized and cleaned (see Japanese Patent Application Publication No. 2005-279648).

However, the above-mentioned article sterilizing method requires a plurality of spraying devices, which may result in a large-scale system. In addition, the distilled water provides insufficient cleaning and thus an insufficient sterilizing effect for the articles.

SUMMARY OF THE INVENTION

The present invention has made to overcome such a conventional problem and it is an object of the invention to provide a sterilizing apparatus which is capable of sterilizing articles, such as test tubes, flasks, beakers, scalpels, forceps and so on, with high efficiency in a short time.

According to a first aspect of the invention, there is provided a sterilizing apparatus for sterilizing articles received in a chamber, including a sterilizing gas generator that supplies sterilizing gas into the chamber.

According to a second aspect of the invention, in the first aspect, the sterilizing gas generator atomizes a sterilizer solution by means of an ultrasonic vibrator.

According to a third aspect of the invention, in the first aspect, the sterilizing gas generator evaporates a sterilizer solution by dipping an absorbing member into the sterilizer solution.

According to a fourth aspect of the invention, in one of the first to third aspects, the sterilizing gas concentration in the cultivating chamber is from 0.1 ppm to 100 ppm.

According to a fifth aspect of the invention, in one of the first to fourth aspects, the sterilizing apparatus further includes an ultraviolet generator that irradiates gas in the chamber with an ultraviolet ray.

According to a sixth aspect of the invention, in the fifth aspect, the sterilizing apparatus further includes a controller that performs a sterilization process for filling the chamber with the sterilizing gas for a predetermined period of time and a decomposition process for decomposing the sterilizing gas by irradiating the gas in the chamber with the ultraviolet ray by means of the ultraviolet generator.

According to a seventh aspect of the invention, in the sixth aspect, the sterilizing apparatus further includes a door for blocking an opening of the chamber in a free-opening/closing manner and a locking device for prohibiting the door from being opened, and the controller controls the locking device to prevent the door from being opened from start of the sterilization process to end of the decomposition process.

According to the first aspect of the invention, since the sterilizing apparatus for sterilizing the articles received in the chamber includes the sterilizing gas generator that supplies the sterilizing gas into the chamber, the sterilizing gas generated by the sterilizing gas generator can be supplied and filled in the chamber in which the articles are received. Accordingly, it is possible to eradicate sundry germs of the articles, including the chamber. Accordingly, it is possible to sterilize the articles in the chamber with high efficiency in a short time.

According to the second aspect of the invention, in the first aspect, since the sterilizing gas generator atomizes the sterilizer solution by means of the ultrasonic vibrator, it is possible to atomize a sundry germs sterilizer and fill the chamber with the atomized sterilizer as a gas without decomposing the sterilizer, unlike a heat and atomization method. Accordingly, it is possible to efficiently sterilize the inside of the apparatus and the articles.

According to the third aspect of the invention, in the first aspect, since the sterilizing gas generator evaporates the sterilizer solution by dipping the absorbing member into the sterilizer solution, it is possible to effectively generate the sterilizing gas to sterilize the articles and the inside of the apparatus while simplifying the configuration of the apparatus.

According to the fourth aspect of the invention, in one of the first to third aspects, since the sterilizing gas concentration in the chamber is from 0.1 ppm to 100 ppm, it is possible to reliably sterilize the articles and the inside of the apparatus.

According to the fifth aspect of the invention, in one of the first to fourth aspects, since the sterilizing apparatus further includes the ultraviolet generator that irradiates gas in the chamber with the ultraviolet ray, it is possible to quickly lower the concentration of the sterilizing gas to a concentration harmless to a human body by decomposing the sterilizing gas using the ultraviolet ray after sterilizing the articles and the inside of the apparatus with the sterilizing gas. Accordingly, it is possible to reduce wait time until the next article sterilizing operation starts.

According to the sixth aspect of the invention, in the fifth aspect, since the sterilizing apparatus further includes the controller that performs the sterilization process for filling the chamber with the sterilizing gas for the predetermined period of time and the decomposition process for decomposing the sterilizing gas by irradiating the gas in the chamber with the ultraviolet ray by means of the ultraviolet generator, it is possible to automate operation from the sterilization of the articles and the inside of the apparatus with the sterilizing gas to the decomposition of the sterilizing gas, thereby remarkably improving workability.

According to the seventh aspect of the invention, in the sixth aspect, since the sterilizing apparatus further includes the door for blocking the opening of the chamber in the free-opening/closing manner and the locking device for prohibiting the door from being opened, and the controller controls the locking device to prevent the door from being opened from start of the sterilization process to end of the decomposition process, it is possible to prevent the door from being opened by mistake before the sterilizing gas concentration is lowered to a value harmless to a human body by the ultraviolet ray after the articles received in the apparatus are sterilized with the sterilizing gas, thereby securing safety of the apparatus.

DETAILED DESCRIPTION OF THE PREFERRED EMBODIMENT

The most important feature of the present invention is to sterilize every corner of a chamber thoroughly and shorten time taken from sterilizing start to sterilizing end for the chamber. The purpose of sterilizing every corner of the chamber thoroughly and shortening time taken from the sterilizing start to the sterilizing end for the chamber can be accomplished by a simple configuration that a sterilizing gas generator is merely provided within the chamber.

Embodiment 1

Figure 1:
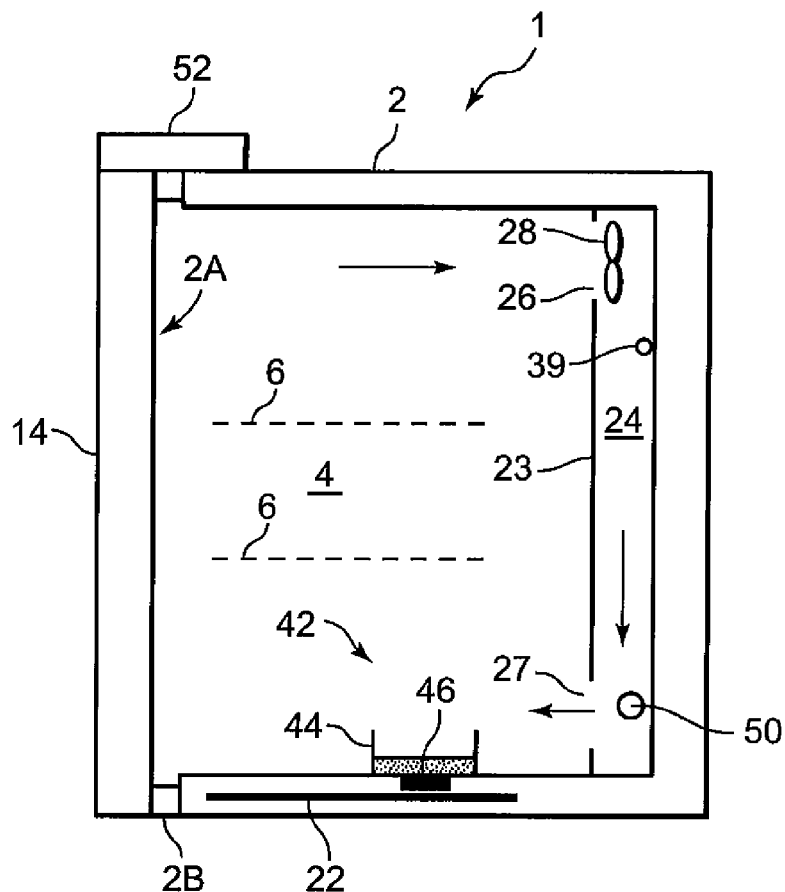
FIG. 1 is an end side view showing a structure of a sterilizing apparatus according to an embodiment (Embodiment 1) of the present invention.
Figure 2:
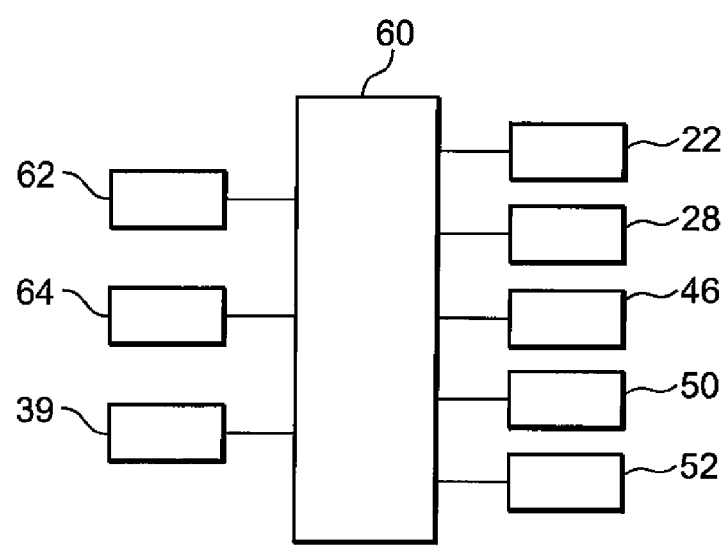
FIG. 2 is a block diagram of a control circuit for controlling the sterilizing apparatus of the present invention.

Hereinafter, embodiments of the present invention will be described with reference to the drawings. FIG. 1 is an end side view showing a structure of a sterilizing apparatus 1 according to an embodiment of the present invention, and FIG. 2 is a block diagram of a control circuit for controlling the sterilizing apparatus 1 of the present invention.

In this embodiment, as shown in FIG. 1, the sterilizing apparatus 1 includes a double-hollow-structured metal (stainless steel) box body 2 having an opening 2A at one side thereof. In addition, the opening 2A of the box body 2 is provided with a door 14 whose right side is supported to the box body 2 by a hinge in a free-opening/closing manner. The door 14 blocks the opening 2A air-tightly by means of a gasket 2B provided in the opening 2A of the box body 2.

A chamber 4 is formed in a space surrounded by the door 14 blocking the opening 2A in a free-opening/closing manner. Within the chamber 4 are provided a plurality (two in this embodiment) of shelves 6 that vertically partitions the chamber 4. Articles received in the chamber 4 are sent in and drawn out of the chamber 4 by opening/closing of the door 14. In addition, the articles may be placed on the shelves 6 either directly or with them put in vessels (not shown).

A heater 22 is arranged in the bottom of the box body 2. When the heater 22 is heated, heat generated from the heater 22 is transferred to the chamber 4, thereby keeping the chamber 4 at a temperature (about +40° C.) appropriate for sterilization.

In addition, a rear wall 23 is provided in the rear side of the chamber 4 and a duct 24 is provided between the rear wall 23 and a rear wall of the box body 2. An inlet 26 communicating to the chamber 4 is provided in the upper side of the duct 24 and an outlet 27 is provided in the lower side of the duct 24. In addition, an air circulation fan 28 for controlling circumferences in the chamber 4 is arranged inside the duct 24 at a position corresponding to the inlet 26.

Air in the chamber 4 is absorbed through the inlet 26 into the duct 24 by means of the fan 28. The absorbed air is discharged through the outlet 27 at the lower side of the duct 24 into the chamber 4 (as indicated by arrows in FIG. 1). Such a configuration allows the air to be forcedly circulated in the chamber 4.

In addition, in the lower side of the chamber 4 of the sterilizing apparatus 1 is provided a sterilizing gas generator 42 to atomize oxygenated water (corresponding to a sterilizer solution in the present invention), and within the duct 24 is provided an oxygenated water measuring sensor 39 to measure oxygenated water gas in the chamber 4. For example, the sterilizing gas generator 42 generates gas by atomizing the oxygenated water as the sterilizer solution in the chamber 4 by means of an ultrasonic wave. The sterilizing gas generator 42 includes a stainless vessel 44 (typically called a butt) provided in the bottom of the box body 2 and an ultrasonic vibrator 46.

The vessel 44 has an opening at top side thereof, which has a size as large as to accommodate the predetermined amount of oxygenated water, and is provided near the front (in the chamber 4) of the outlet 27 of the duct 24. In addition, the bottom of the vessel 44 is depressed into the bottom of the box body 2 and the ultrasonic vibrator 46 is provided within the depressed vessel 44. In addition, when the oxygenated water is evaporated by a heating type humidifier which is currently frequently being used, since hydrogen peroxide (sterilizer) is decomposed, the ultrasonic vibrator 46 is attached to the bottom of the chamber 4 (the bottom of the box body 2) in the present invention. The ultrasonic vibrator 46 can atomize the hydrogen peroxide without heating it. Since a technique for the ultrasonic vibrator 46 to atomize the hydrogen peroxide without heating it is well known in the art, explanation of which will be omitted.

An ultraviolet lamp 50 (corresponding to an ultraviolet generator in the present invention) for generating an ultraviolet ray is arranged in the sterilizing apparatus 1. The ultraviolet ray emitted from the ultraviolet lamp 50 decomposes the sterilizing gas circulating in the duct 24, thereby making it harmless. To make the sterilizing gas harmless by the ultraviolet lamp 50 will be described in detail later.

When the oxygenated water is atomized and gasified by the ultrasonic wave to sterilize the articles received in the sterilizing apparatus 1, if the door 14 is carelessly opened, the sterilizing gas is get out of the chamber 4, which may result in danger to a human body. So, in the present invention, the sterilizing apparatus 1 includes a locking device 52 to prevent the door 14 from being released while the chamber 4 is sterilized with the oxygenated water. The locking device 52 is provided in the top side of the box body 2, spanning between the top side of the box body 2 and the top side of the door 14. The locking device 52 is fixed to the box body 2, and in this state, the door 14 is configured to be openable/closable and the door 14 is configured to be locked/unlocked with the locking device 52.

In the meantime, as shown in FIG. 2, the sterilizing apparatus 1 is provided with a controller 60. The controller 60 is, for example, a general-purpose microcomputer including a storing unit (memory) in which data can be stored, a timer, etc. The controller 60 is connected with an operation switch such as a power switch or a sterilization start switch (not shown), a temperature sensor 64 for detecting the internal temperature of the chamber 4, an oxygenated water measuring sensor 39, etc.

In addition, the controller 60 is connected with the ultraviolet lamp 50 for sterilization of circulation air, the air circulation fan 28 for controlling the circumferences in the chamber 4, etc. In addition, the controller 60 is connected with the heater 22 for heating the chamber 4 at a temperature appropriate for sterilization, the ultrasonic vibrator 46 for atomizing the oxygenated water, the locking device 52 for preventing the door 14 from being released, etc.

The controller 60 has programs for a sterilization process for sterilizing the chamber 4 and a decomposition process for decomposing the sterilizing gas in the chamber 4 with the ultraviolet lamp 50 after the sterilization process, which are stored in the memory of the microcomputer.

Next, with the above configuration, the operation of the sterilizing apparatus 1 will be described. In particular, in this embodiment, the sterilization process and the decomposition process of the sterilizing apparatus 1 will be described. Here, it is assumed that articles to be sterilized, such as test tubes, flasks, beakers, scalpels, forceps and so on, are beforehand placed on the shelves 6 in the chamber 4. In the sterilization process of the sterilizing apparatus 1, first, when the operation switch 62 (the sterilization start switch) is pushed by an operator, the controller 60 drives the locking device 52 to lock the door 14 and drives the fan 28. Accordingly, the air in the chamber 4 is absorbed into the duct 24 through the inlet 26 and is discharged into the chamber 4 from the bottom of the duct 24, circulating in the chamber 4 (see arrows indicated in FIG. 1).

The controller 60 operates the fan 33 and, at the same time, heats the heater 22. Then, the controller 60 detects the temperature of the chamber 4 by means of the temperature sensor 64, and keeps the chamber 4 at a predetermined temperature (about +40° C.). Moreover, the controller 60 automatically interrupts the heat from the heater 22 after the decomposition process.

Next, the controller 60 drives the ultrasonic vibrator 46 with a preset timer for a predetermined period of time to atomize the oxygenated water in the vessel 44 and scatter the atomized oxygenated water into the chamber 4. As the chamber 4 is heated with the heater 22 at the predetermined temperature, the oxygenated water atomized and scattered into the chamber 4 is evaporated in a short time to be hydrogen peroxide gas with which the chamber 4 is filled. At this time, since the vessel 44 is filled with a predetermined amount of oxygenated water, the chamber 4 has hydrogen peroxide gas concentration of from 0.1 ppm to 100 ppm. The amount of oxygenated water in the vessel 44 is beforehand obtained by experiment such that the hydrogen peroxide gas concentration in the chamber 4 is from 0.1 ppm to 100 ppm.

The hydrogen peroxide gas evaporated in the chamber 4 is circulated every corner of the chamber 4 by the fan 28. Accordingly, all the inside of the sterilizing apparatus 1 including the chamber 4 can be sterilized with the oxygenated water gas with efficiency.

In addition, since the oxygenated water supplied and stored in the vessel 44 is atomized and then evaporated, the articles received in the sterilizing apparatus 1 can be sterilized with efficiency. In addition, since the ultrasonic vibrator 46 to atomize the oxygenated water does not heat and evaporate the oxygenated water, it is possible to atomize a sundry germs sterilizer without decomposing it, unlike the heat and atomization.

After performing the sterilization process for a predetermined period of time, the controller 60 stops the ultrasonic vibrator 46 and turns on the ultraviolet lamp 50 provided in the duct 24 for transfer to the decomposition process. The controller 60 performs the sterilization process and the decomposition process in an automatic sequential manner. In the decomposition process, since the controller 60 operates the fan 28 and turns on the ultraviolet lamp 50, the hydrogen peroxide gas inside the sterilizing apparatus 1 is circulated to the ultraviolet lamp 50 and is decomposed by irradiation of the ultraviolet lamp 50. According to a decomposition reaction of the hydrogen peroxide, $H_2O_2 \rightarrow OH$ radicals$\rightarrow H_2O$, the hydrogen peroxide finally turns to harmless water.

The controller 60 continues to perform the decomposition process for the hydrogen peroxide gas by the ultraviolet ray from the ultraviolet lamp 50 until the concentration of the hydrogen peroxide gas in the chamber 4, which is detected by the oxygenated water measuring sensor 39, is lowered to a harmless value. Accordingly, since the concentration of the hydrogen peroxide gas in the sterilizing apparatus 1 can be quickly lowered to a value harmless to a human body, it is possible to significantly reduce wait time until the next cultivation operation starts.

When the decomposition process is completed, the controller 60 drives the locking device 52 to release the lock of the door 14. In this case, as the hydrogen peroxide gas (sterilizing gas) in the chamber 4 is forcedly decomposed with the ultraviolet ray, it is possible to significantly shorten the wait time till the next article sterilizing operation, as compared to a natural decomposition. Accordingly, it is possible to smoothly sterilize the articles received in the chamber 4 in a short time. In addition, until the decomposition process is ended from the sterilization process in the sterilizing apparatus 1, the controller 60 prohibits the door 14 from being opened by means of the locking device 52. Accordingly, it is possible to prevent the door 14 from being opened by mistake before the sterilizing gas concentration is lowered to a value harmless to a human body by the ultraviolet ray after the articles received in the sterilizing apparatus 1 is sterilized with the sterilizing gas. Thus, when the articles received in the chamber 4 are sterilized with the sterilizing gas, it is possible to secure substantial safety of the sterilizing apparatus 1.

Embodiment 2

Figure 3:
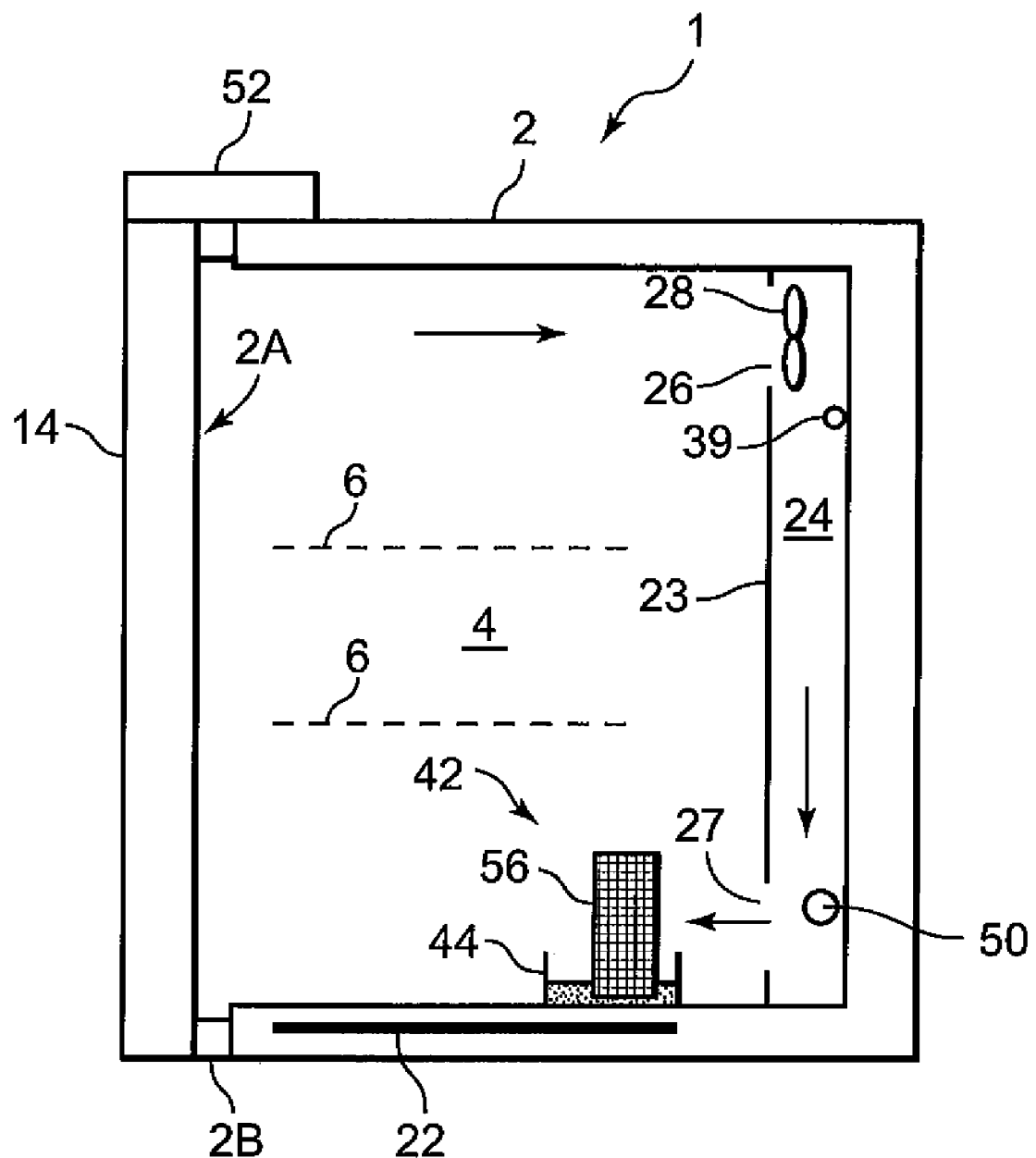
FIG. 3 is an end side view showing a structure of a sterilizing apparatus according to another embodiment (Embodiment 2) of the present invention.

Next, FIG. 3 shows a sterilizing apparatus 1 according to another embodiment of the present invention. The sterilizing apparatus 1 of this embodiment has substantially the same configuration as the above-described embodiment. Hereinafter, only portions different from the above-described embodiment will be described. In the figure, the same elements as the above-described embodiment are denoted by the same reference numerals, and explanation of which will be omitted. As shown in FIG. 3, in the sterilizing apparatus 1, the ultrasonic vibrator 46 of the sterilizing gas generator 42 in Embodiment 1 is replaced with an absorbing member 56. When the absorbing member 56 is dipped into oxygenated water, the oxygenated water is evaporated.

That is, the sterilizing gas generator 42 is provided with the absorbing member 56 erecting in the vessel 44 having flat bottom. A frame (not shown) made of stainless steel or synthetic resin is provided around the absorbing member 56. A given wide nonwoven fabric or the like to suck up the oxygenated water according to a capillary effect is fixed in the frame.

In more detail, the vessel 44 is provided near the front side (in the chamber 4) of the outlet 27 as described above, and the frame attached with the absorbing member 56 is erected and fixed in the bottom of the vessel 44. With this configuration, air discharged from the duct 24 through the outlet 27 makes direct contact with the absorbing member 56 and the oxygenated water is evaporated from the absorbing member 56 to properly sterilize the chamber 4. In addition, the hydrogen peroxide gas concentration in the chamber 4 is measured using a hydrogen peroxide measuring test paper put in the chamber 4.

In this manner, in the sterilizing gas generator 42, the absorbing member 56 is dipped into the oxygenated water, and circulating air contacts the absorbing member 56 for a predetermined period of time set by a timer controlled by the controller 60. Thus, the oxygenated water is evaporated and the chamber 4 is filled with the evaporated oxygenated water. Accordingly, it is possible to effectively generate the sterilizing gas to sterilize the inside of the sterilizing apparatus 1. In particular, since the absorbing member 56 is merely erected in the vessel 44 filled with the oxygenated water, it is possible to significantly simplify the sterilizing gas generator 42.

Although it has been illustrated in the above embodiments that the sterilizing gas generator 42 is provided within the chamber 4 of the sterilizing apparatus 1, without being limited to this, the sterilizing gas generator 42 may be provided outside the sterilizing apparatus 1 instead of inside the chamber 4. In addition, although the hydrogen peroxide has been used as the sterilizer, without being limited to the hydrogen peroxide, the sterilizer may be of any type as long as it can have sterilizing power.

In addition, although it has been illustrated that the box body 2 of the sterilizing apparatus 1 has the double-hollowed structure, without being limited to this, the box body 2 may be formed of a single metal plate. In this case, the heater 22 is provided within the box body 2, and the vessel 44 of the sterilizing gas generator 42, which has the same flat bottom as in Embodiment 2, is used. Accordingly, it is possible to properly sterilize the chamber 4, thereby obtaining the same effects as the above embodiments. In addition, only the bottom of the box body 2 may have a double structure.

The present invention is not limited to the above-described embodiments but may be effectively changed and modified in various ways without departing from the spirit and scope of the invention.

What is claimed is:

1. A sterilizing apparatus for sterilizing articles received in a chamber, comprising (a) a sterilizing gas generator that supplies sterilizing gas into the chamber, selected from one of a generator that atomizes a sterilizer solution by means of an ultrasonic vibrator and a gas generator that evaporates a sterilizer solution by dipping an absorbing member into the sterilizer solution, and (b) an ultraviolet generator that irradiates gas in the chamber with an ultraviolet ray;

the chamber enclosed by a box-body having a rear wall spaced from a rear wall of the box body to form a duct having an inlet communicating with the chamber provided at an upper side of the duct and having a circulating fan inside the duct at the inlet, an outlet provided at a lower side of the duct, with the ultraviolet generator arranged to decompose sterilizing gas circulating in the duct;

a controller that performs a sterilization process for filling the chamber with the sterilizing gas for a predetermined period of time and a decomposition process for decomposing the sterilizing gas by irradiating the gas in the chamber with the ultraviolet ray by means of the ultraviolet generator, and a door for blocking an opening of the chamber in a free-opening/closing manner and a locking device for prohibiting the door from being opened, wherein the controller controls the locking device to prevent the door from being opened from start of the sterilization process to end of the decomposition process.

2. The sterilizing apparatus according to claim 1, wherein the sterilizing gas concentration in the chamber is from 0.1 ppm to 100 ppm.

* * * * *